United States Patent [19]

Christensen et al.

[11] 4,372,965
[45] Feb. 8, 1983

[54] 6-, 1- AND 2-SUBSTITUTED-THIO-1-CARBADETHIAP-EN-2-EM-3-CARBOXYLIC ACID S-OXIDES

[75] Inventors: Burton G. Christensen, Scotch Plains; David H. Shih, Manalapan, both of N.J.

[73] Assignee: Merck & Co., Inc., Rahway, N.J.

[21] Appl. No.: 223,505

[22] Filed: Jan. 8, 1981

Related U.S. Application Data

[63] Continuation-in-part of Ser. No. 84,932, Oct. 15, 1979, abandoned.

[51] Int. Cl.³ .................... C09D 487/04; H61K 31/40
[52] U.S. Cl. ........................... 424/274; 260/245.2 T; 424/263; 424/269; 424/270
[58] Field of Search ................ 260/245.2 T; 424/274; 546/272

[56] References Cited

U.S. PATENT DOCUMENTS

| | | | |
|---|---|---|---|
| 4,123,547 | 10/1978 | Christensen et al. | 260/245.2 T |
| 4,150,145 | 4/1979 | Christensen et al. | 260/245.2 T |
| 4,181,733 | 1/1980 | Christensen et al. | 260/245.2 T |
| 4,218,462 | 8/1980 | Christensen et al. | 260/245.2 T |
| 4,232,036 | 11/1980 | Christensen et al. | 260/245.2 T |
| 4,341,791 | 7/1982 | Christensen et al. | 260/245.2 T |

*Primary Examiner*—Mary C. Lee
*Attorney, Agent, or Firm*—James A. Arno; Hesna J. Pfeiffer

[57] ABSTRACT

Disclosed are S-oxides of 6-, 1- and 2-substituted-1-carbadethiapen-2-em-3-carboxylic acids having the structure:

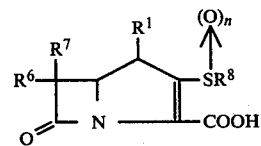

wherein: n is 1 or 2; and $R^1$, $R^6$, $R^7$ and $R^8$ are, *inter alia*, independently selected from the group consisting of hydrogen, alkyl, alkenyl, aryl and aralkyl. Such compounds as well as their pharmaceutically acceptable salt, ester and amide derivatives are useful as antibiotics. Also disclosed are processes for the preparation of such compounds, pharmaceutical compositions comprising such compounds and methods of treatment comprising administering such compounds and compositions when an antibiotic effect is indicated.

8 Claims, No Drawings

6-, 1- AND 2-SUBSTITUTED-THIO-1-CARBADETHIAPEN-2-EM-3-CARBOXYLIC ACID S-OXIDES

BACKGROUND OF THE INVENTION

This is a continuation-in-part of U.S. Ser. No. 84,932 filed Oct. 15, 1979 now abandoned.

This invention relates to S-oxides of 6-, 1- and 2-substituted-1-carbadethiapen-2-em-3-carboxylic acids and derivatives thereof which are useful as antibiotics and which may be represented by the following generic structural formula (I):

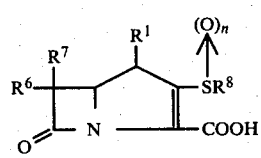

wherein: n is 1 or 2; and $R^1$, $R^6$, $R^7$ and $R^8$ are independently selected from the group consisting of hydrogen, substituted and unsubstituted: alkyl, alkenyl, and alkynyl, having from 1-10 carbon atoms; cycloalkyl, cycloalkylalkyl, and alkylcycloalkyl, having 3-6 carbon atoms in the cycloalkyl ring and 1-6 carbon atoms in the alkyl moieties; aryl, such as phenyl; aralkyl, aralkenyl, and aralkynyl wherein the aryl moiety is phenyl and the linear chain has 1-6 carbon atoms; heteroaryl, heteroaralkyl, heterocyclyl and heterocyclylalkyl; wherein the substituent or substituents relative to the above-named radicals are selected from the group consisting of: amino, mono, di- and trialkylamino, hydroxyl, alkoxyl, mercapto, alkylthio, arylthio such as phenylthio, sulfamoyl, amidino, guanidino, nitro, chloro, bromo, fluoro, cyano and carboxy; and wherein the hetero atom or atoms in the above-named heterocyclic moieties are selected from the group consisting of 1-4 oxygen, nitrogen or sulphur atoms; and wherein the alkyl moieties of the above-recited substituents have 1-6 carbon atoms.

This invention also relates to the carboxyl derivatives of I which are antibiotics and which may be represented by the following generic structure (I):

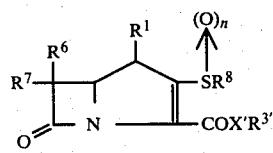

wherein X' is oxygen, sulphur or NR' (R'=H or lower alkyl having 1-6 carbon atoms); and $R^{3'}$ is, inter alia, representatively selected from the group consisting of hydrogen, conventional blocking groups which as trialkylsilyl, acyl and the pharmaceutically acceptable salt, ester and amide moieties known in the bicyclic β-lactam antibiotic art; the definition of $R^{3'}$ is given in greater detail below.

This invention also relates to processes for the preparation of such compounds (I); pharmaceutical compositions comprising such compounds; and to methods of treatment comprising administering such compounds and compositions when an antibiotic effect is indicated.

There is a continuing need for new antibiotics. For unfortunately, there is no static effectiveness of any given antibiotic because continued wide scale usage selectively gives rise to resistant strains of pathogens. In addition, the known antibiotics suffer from the disadvantage of being effective only against certain types of microorganisms. Accordingly the search for new antibiotics continues.

Thus, it is an objection of the present invention to provide a novel class of antibiotics which are useful in animal and human therapy and in inanimate systems. These antibiotics are active against a broad range of pathogens which representaively include both gram positive bacteria such as *S. aureus, Strep. pyogenes,* and *B. subtilis,* and gram negative bacteria such as *E. coli,* Pseudomonas, *Proteus morganii,* Serratia, and Klebsiella. Further objects of this invention are to provide chemical processes for the preparation of such antibiotics and their non-toxic pharmaceutically acceptable salts; pharmaceutical compositions comprising such antibiotics; and to provide methods of treatment comprising administering such antibiotics and compositions when an antibiotic effect is indicated.

Relative to Structure I, the following classes are especially preferred:

Class 1.

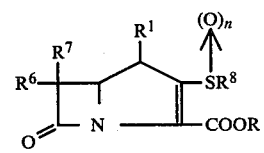

and the pharmaceutically acceptable salts thereof; wherein R is H, a pharmaceutically acceptable salt catpharmaceutically acceptable ester moiety; and $R^1$, $R^6$, $R^7$ and $R^8$ are independently selected from the group consisting of hydrogen, ($R^1$ is not H) substituted and unsubstituted: alkyl, alkenyl, and alkynyl, having from 1-10 carbon atoms; cycloalkyl, cycloalkylalkyl, and alkylcycloalkyl, having 3-6 carbon atoms in the cycloalkyl ring and 1-6 carbon atoms in the alkyl moieties; phenyl; aralkyl, aralkenyl, and aralkynyl wherein the aryl moiety is phenyl and the alkyl chain has 1-6 carbon atoms; heteroaryl, heteroaralkyl, heterocyclyl and heterocyclylalkyl wherein the substituents or substituents relative to the above-named radicals are selected from the group consisting of: amino, mono-, di-, and trialkylamino, hydroxyl, alkoxyl, mercapto, alkylthio, phenylthio, sulfamoyl, amidino, guanidino, nitro, chloro, bromo, fluoro, cyano and carboxy; and wherein the hetero atom or atoms in the above-named heterocyclic moieties are selected from the group consisting of 1-4 oxygen, nitrogen or sulphur atoms; and wherein the alkyl moieties of the above-recited substituents have 1-6 carbon atoms; n is 1 or 2.

Class 2. A compound according to Class 1 wherein $R^1$ is alkyl, phenyl, benzyl or cycloalkyl.

Class 3. A compound according to Class 1 wherein $R^6$ is H or methyl and $R^7$ is alkyl, phenyl, aralkyl or hydroxyl-substituted alkyl, phenyl or aralkyl.

Class 4. A compound according to Class 1 wherein: n is 1; $R^6$ is hydrogen or methyl and $R^8$ is selected from the group consisting of:

H,
CH₃,
(CH₂)₂NH₂,
C(CH₃)₂CH₂NH₂,

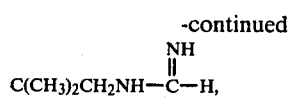
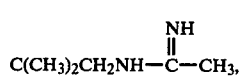
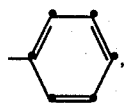
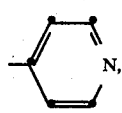
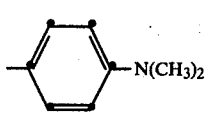
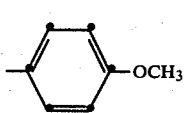
CH₂CH₂CH₂NH₂,
CH₂CH(CH₃)NH₂,
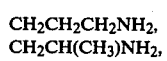
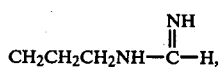
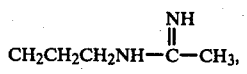
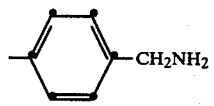
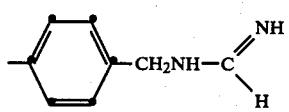
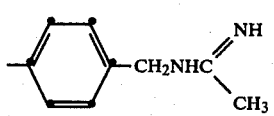
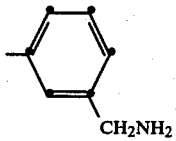
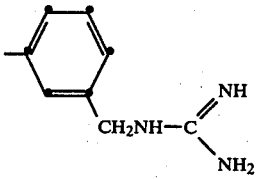
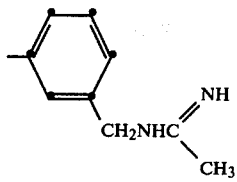
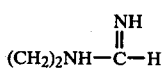
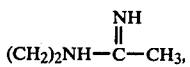
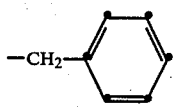
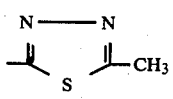
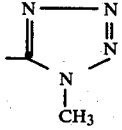
CH(CH₃)CH₂NH₂,
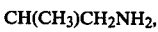 or
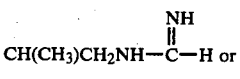
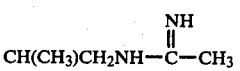
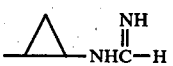
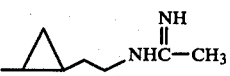
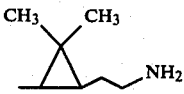
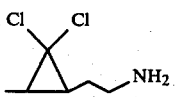
and R⁷ is selected from:
—CH₂OH

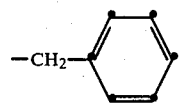

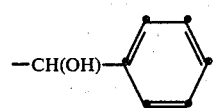

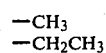

Class 5. A compound according to Class 4 wherein $R^1$ is methyl, ethyl, isopropyl, phenyl, benzyl, cyclopropyl, or cyclopropylmethyl.

Class 6. A compound according to Class 1 having the structure:

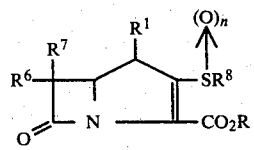

and the pharmaceutically acceptable salts thereof wherein R is H; pharmaceutically acceptable salt cation; or a pharmaceutically acceptable ester moiety; and $R^6$, $R^7$ and $R^8$ are independently selected from the group consisting of hydrogen, substituted and unsubstituted: alkyl, alkenyl, and alkynyl, having from 1–10 carbon cycloalkyl, cycloalkylalkyl, and alkylcycloalkyl, having 3–6 carbon atoms in the cycloalkyl ring and 1–6 carbon atoms in the alkyl moieties; phenyl; aralkyl, aralkenyl, and aralkynyl wherein the aryl moiety is phenyl and the alkyl chain has 1–6 carbon atoms; wherein the substituent or substituents relative to the above-named radicals are selected from the group consisting of: amino, mono-, di- and trialkylamino, hydroxyl, alkoxyl, mercapto, alkylthio, phenylthio, sulfamoyl, amidino, guanidino, nitro, chloro, bromo, fluoro, cyano and carboxy; and wherein the alkyl moieties of the above-recited substituents have 1–6 carbon atoms; and $R^1$ is selected from the group consisting of methyl, ethyl, propyl, isopropyl cyclopropyl, phenyl and benzyl.

DETAILED DESCRIPTION OF THE INVENTION

The compounds of the present invention (I, above) are conveniently prepared by the following scheme:

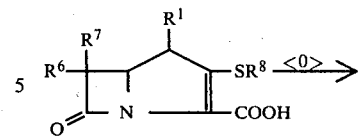

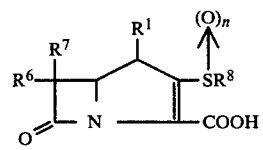

Relative to the above reaction scheme, it is recognized that the sulfoxide (n=1) is quantitatively obtained when one equivalent of the oxidizing agent, [0], is taken; whereas two equivalents provide the sulphone embodiment (n=2). There is no criticality as to the precise identity of the oxidizing agent. Suitable oxidizing agents include peracids such as m-chloroperbenzoic acid and peracetic acid; other representative oxidizing agents include potassium permanganate, hydrogen peroxide, and ozone, for example. There is no criticality as to reaction solvent—any solvent being acceptable which is inert or substantially inert during the course of reaction and which effectively solubilizes the starting material 1. Representative examples of suitable solvents for the oxidation include tetrahydrofuran, methylenechloride, and water. Typically, the reaction is conducted at a temperature of from about 0° to about 50° C., for from a few minutes to about one hour for the sulfoxide and, for the sulfone, 1 to 6 hours.

Starting materials 1 are described and claimed in copending, commonly assigned U.S. patent application Ser. No. 865,165 (filed Dec. 28, 1977 now U.S. Pat. No. 4,218,463) and Ser. No. 030,786 (filed Apr. 17, 1979 now U.S. Pat. No. 4,224,336). To the extent that the foregoing, copending U.S. patent applications define starting materials 1 and their preparation, they are hereby incorporated by reference. Also incorporated by reference is U.S. Pat. No. 4,123,547 issued Oct. 31, 1978. This patent describes and claims thienamycin sulfoxide and thienamycin sulfone. The patent describes an oxidation procedure for obtaining those species from thienamycin, which procedure is analogous to the instant oxidation of 1 to form I. To the extent that U.S. Pat. No. 4,123,457 describes an oxidation procedure for the oxidation of thienamycin to its corresponding sulfoxide and sulphone, it is hereby incorporated by reference.

The products of this invention (I) form a wide variety of pharmacologically acceptable salts with inorganic and organic bases; these include, for example, metal salts derived from alkali or alkaline earth metal hydroxides, carbonates or bicarbonates and salts derived from primary, secondary or tertiary amines such as monoalkylamines, dialkylamines, trialkylamines, lower alkanolamines, di-lower-alkanolamines, lower alkylenediamines, N,N-diaralkyl lower alkylenediamines, aralkylamines, amino substituted lower alkanols, N,N-di-lower alkylamino substituted lower alkanols, amino-, polyamino- and guanidino-substituted lower alkanoic acids and nitrogen-containing heterocyclic amines. Representative examples include salts derived from sodium hydroxide, sodium carbonate, sodium bicarbonate, potassium carbonate, potassium hydroxide, calcium carbonate, trimethylamine, triethylamine, piperidine, morpholine, quinine, lysine, protamine, arginine, procaine, ethanolamine, morphine, benzylamine, ethylenediamine, N,N'-dibenzylethylenediamine, diethanolamine, piperazine, dimethylaminoethanol, 2-amino-2-methyl-1-propanol, theophylline, N-methylglucamine and the like. Acid addition salts, e.g, with hydrochloric, tartaric, hydrobromic, sulfuric, nitric, toluene-p-sulphonic and methane sulphonic acids may also be employed.

The salts can be mono-salts such as the monosodium salt obtained by treating one equivalent of sodium hydroxide with one equivalent of the product (I), also mixed di-salts. Such salts may be obtained by treating one equivalent of a base having a divalent cation, such as calcium hydroxide, with one equivalent of the product (I). The salts of this invention are pharmacologically acceptable nontoxic derivatives which can be used as the active ingredient in suitable unit-dosage pharmaceutical forms. Also, they may be combined with other drugs to provide compositions having a broad spectrum of activity.

The compounds of the present invention are valuable antimicrobial substances which are active against various gram-positive and gram-negative pathogens. Thus the free acid, free base, and especially the salts thereof such as amine and metal salts, particularly the alkali metal and alkaline earth metal salts, are useful bactericides and can be used for removing susceptible pathogens from dental and medical equipment, for separating microorganisms, and for therapeutic use in humans and animals. For this latter purpose pharmacologically acceptable salts with inorganic and organic bases such as those known in the art and used for the administration of penicillins and cephalosporins can be utilized. For example, salts such as alkali metal and alkaline earth metal salts, and primary, secondary and tertiary amine salts can be used for this purpose. These salts can be combined with pharmaceutically acceptable liquid and solid vehicles to form suitable dosage unit forms such as pills, tablets, capsules, suppositories, syrups, elixirs and the like which can be prepared in accordance with procedures well known in this art.

The novel compounds are valuable antibiotics active against various gram-positive and gram-negative bacteria, and accordingly, find utility in human and veterinary medicine. The compounds of this invention can therefore be used as antibacterial drugs for treating infections caused by gram-positive or gram-negative bacteria, for example against *Staphylococcus aureus, Escherichia coli, Klebsiella pneumoniae, Bacillus substilis, Salmonella typhosa,* Pseudomonas and *Bacterium proteus.* The antibacterials of the invention may further be utilized as additives to animal feedingstuffs, for preserving foodstuffs and disinfectants. For example, they may be employed in aqueous compositions in concentrations ranging from 0.1 to 100 parts of antibiotic per million parts of solution in order to destroy and inhibit the growth of harmful bacteria on medical and dental equipment and as bactericides in industrial applications, for example in waterbased paints and in the white water of paper mills to inhibit the growth of harmful bacteria.

The products of this invention may be used alone or in combination as an active ingredient in any one of a variety of pharmaceutical preparations. These antibiotics and their corresponding salts may be employed in capsule form or as tablets, powders or liquid solutions or as suspensions or elixirs. They may be administered orally, intravenously or intramuscularly.

The compositions are presented in a form suitable for absorption by the gastrointestinal tract. Tablets and capsules for oral administration may be in unit dose presentation form, and may contain conventional excipients such as binding agents, for example, syrup, acacia, gelatin, sorbitol, tragacanth, or polyvinylpyrrolidone; fillers for example, lactose, sugar, maizestarch, calcium phosphate, sorbitol or glycine; lubricants, for example, magnesium stearate, talc, polyethylene glycol, silica; disintegrants, for example, potato starch or acceptable wetting agents such as sodium lauryl sulphate. The tablets may be coated according to methods well known in the art. Oral liquid preparations may be in the form of aqueous or oily suspension solution, emulsions, syrups, elixirs, etc. or may be presented as a dry product, for reconstitution with water or other suitable vehicles before use. Such liquid preparations may contain conventional additives such as suspending agents, for example, sorbitol syrup, methyl cellulose, glucose/sugar syrup, gleatin, hydroxyethylcellulose, carboxymethyl cellulose, aluminum stearate gel or hydrogenated edible oils, for example almond oil, fractionated coconut oil, oily esters, propylene glycol, or ethyl alcohol; preservatives, for example methyl or propyl p-hydroxybenzoates or sorbic acid. Suppositories will contain conventional suppository bases, e.g. cocoa butter or other glyceride.

Compositions for injection may be presented in unit dose form in ampules, or in multidose containers with an added preservative. The compositions may take such forms as suspensions, solutions, or emulsions in oily or aqueous vehicles, and may contain formulatory agents such as suspending stabilizing and/or dispersing agents. Alternatively, the active ingredient may be in powder form for reconstitution with a suitable vehicle, e.g., sterile, pyrogen-free water, before use.

The compositions may also be prepared in suitable forms for absorption through the mucous membranes of the nose and throat or bronchial tissues and may conveniently take the form of powder or liquid sprays or inhalants, lozenges, throat paints, etc. For medication of the eyes or ears, the preparations may be presented as individual capsules, in liquid or semi-solid form, or may be used as drops. Topical applications may be formulated in hydrophobic or hydrophilic bases such as ointments, creams, lotions, paints, powders.

Also, in addition to a carrier, the instant compositions may include other ingredients such as stabilizers, binders, antioxidants, preservatives, lubricators, suspending agents, viscosity agents or flavoring agents and the like. In addition, there may also be included in the composition other active ingredients to provide a broader spectrum of antibiotic activity.

For veterinary medicine the composition may, for example, be formulated as an intramammary preparation in either long acting or quick-release bases.

The dosage to be administered depends to a large extent upon the condition of the subject being treated and the weight of the host, the route and frequency of administration, the parenteral route being preferred for generalized infections and the oral route for intestinal infections. In general, a daily oral dosage consists of from about 5 to about 600 mg. of active ingredient per kg. of body weight of the subject in one or more applications per day. A preferred daily dosage for adult humans lies in the range of from about 15 to 240 mg. of active ingredient per kg. of body weight.

The instant compositions may be administered in several unit dosage forms as, for example, in solid or liquid orally ingestible dosage form. The compositions per unit dosage, whether liquid or solid may contain from 0.1% to 99% of active material, the preferred range being from about 10–60%. The composition will generally contain from about 15 mg. to about 1500 mg. of the active ingredient; however, in general, it is preferable to employ a dosage amount in the range of from about 250 mg. to 1000 mg. In parenteral administration the unit dosage is usually the pure compound in a slightly acidified sterile water solution or in the form of a soluble powder intended for solution.

The following examples, illustrate but do not limit the product, process, compositional or method of treatment aspects of the present invention. All reaction temperatures are in 0° C.

EXAMPLE 1

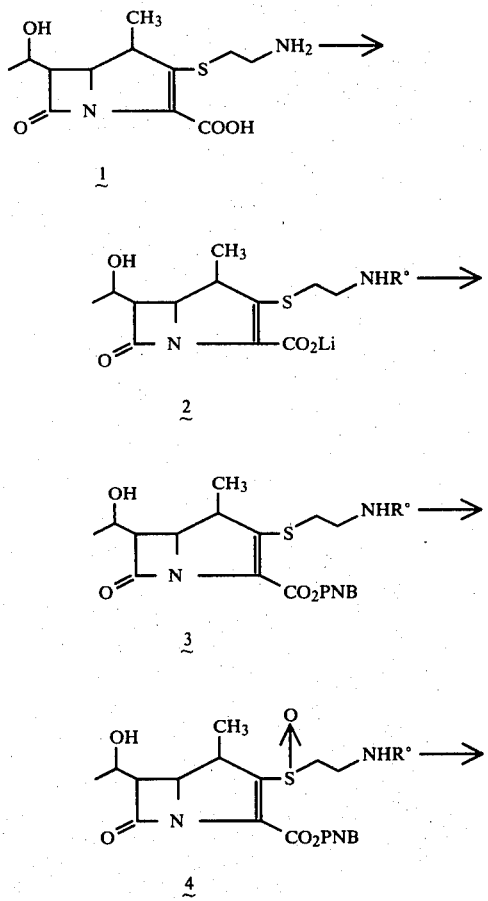

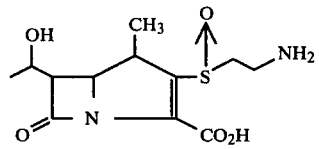

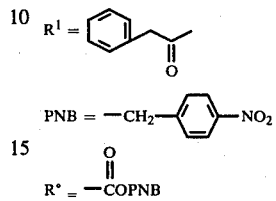

PNB = —CH$_2$—⟨⟩—NO$_2$

R* = —COPNB

STEP A

Starting material 1 (0.51 mmol) is dissolved in ice-cold H$_2$O (35 ml) and the solution is treated with NaHCO$_3$ (428 mg, 5.1 mmol). Dioxane (35 ml) is then added with stirring and ice-bath cooling. After 3 mins, a solution of p-nitrobenzyl chloroformate (165 mg, 0.765 mmol) in dioxane (2 ml) is added dropwise over 2 mins. The resulting mixture is stirred in the cold for 10 mins and then extracted with ice-cold Et$_2$O (2×20 ml). The aqueous phase is separated, layered with ice-cold EtOAc (35 ml), and acidified to pH 2.3 with 1 MH$_2$SO$_4$ while vigorously stirring in an ice-bath. The layers are separated and the aqueous portion extracted with more cold EtOAc (2×5 ml). The combined EtOAc extracts are washed with ice-cold brine and then extracted thoroughly with 0.05 N aq. LiOH (10 ml). The LiOH extract is rotary evaporated to remove EtOAc and then lyophilized to provide the crude N-(p-nitrobenzyloxycarbonyl) lithium salt.

A portion of the crude lithium carboxylate (250 mg) and p-nitrobenzyl bromide (373 mg, 1.73 mmol) in anhydrous HMPA (2.65 ml) are stirred at room temperature (25° C.) for 105 mins. The mixture is diluted with EtOAc (60 ml), washed with H$_2$O (2×50 ml), 5% NaHCO$_3$ (25 ml), H$_2$O (2×25 ml), and brine (25 ml), dried with MgSO$_4$, filtered, and evaporated in vacuo (i.v.). This material is triturated with Et$_2$O to remove excess p-nitrobenzyl bromide and the remaining solids are filtered off and dried i.v. to yield 3. [Relative to the above text, Et$_2$O symbolizes diethylether and EtOAc is ethylacetate.]

STEP B

Intermediate 3 (0.20 mmol) is dissolved in anhydrous tetrahydrofuran (6.0 ml) and the solution is stirred under a nitrogen atmosphere with ice-bath cooling. A solution of 85% m-chloroperbenzoic acid (44.7 mg, 0.22 mmol) in anhydrous methylene chloride (2.0 ml) is added dropwise over 8 mins to the solution. The resulting solution is stirred in the cold an additional 12 mins, then diluted with ethyl acetate (20 ml), washed with 5% sodium bicarbonate (2×10 ml) and brine, dried with magnesium sulfate, filtered, and concentrated under reduced pressure to provide the crude sulfoxide 4. The crude product is triturated with ethyl acetate (2×2 ml) and ethyl ether (2×4 ml) and dried in vacuo to yield substantially pure 4.

STEP C

Protected intermediate 4 (25 mg) is dissolved in dioxane (3.0 ml) and the solution is treated with 10% palladium on powdered charcoal (25 mg), ethanol (0.25 ml), 1 M dipotassium hydrogen phosphate (0.05 ml), and deionized water (1.75 ml). The resulting mixture is hydrogenated on a Parr shaker for 1 hr. The catalyst is removed by centrifugation and washed with 0.1 M pH 7 phosphate buffer (1 ml) and water (1 ml). The combined superantants are washed with ethyl acetate (3×3 ml), concentrated in vacuo to 1 ml, and charged onto a Dowex 50-X4 column (1.4×20 cm, sodium form). The column is eluted with deionized water. The progress of the chromatograph is monitored by UV and HPLC to identify fractions comprising I, which are pooled and lyophilized to yield I.

EXAMPLE 2

Preparation of Pharmaceutical Compositions

One such unit dosage form consists in mixing an equimolar mixture of I:

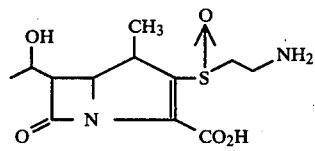

with 20 mg of lactose and 5 mg of magnesium stearate and placing the 145 mg mixture into a No. 3 gelatin capsule. Similarly, by employing more of the active ingredient and less lactose, other dosage forms can be put up in No. 3 gelatin capsules and should it be necessary to mix more than 145 mg of ingredients together, larger capsules such as compressed tablets and pills can also be prepared. The following examples are illustrative of the preparation of pharmaceutical formulations:

| TABLET | PER TABLET |
|---|---|
| I | 125 mg. |
| Cornstarch, U.S.P. | 6 mg. |
| Dicalcium Phosphate | 192 mg. |
| Lactose, U.S.P. | 190 mg. |
| Magnesium Stearate | Balance/800 mg. |

The active ingredient is blended with the dicalcium phosphate, lactose and about half of the cornstarch. The mixture is then granulated with 15% cornstarch paste (6 mg) and rough-screened. It is dried at 45° C. and screened again through No. 16 screens. The balance of the cornstarch and magnesium stearate is added and the mixture is compressed into tablets, approximately 0.5 inch in diameter each weighing 800 mg.

| PARENTERAL SOLUTION | PER TABLET |
|---|---|
| Ampoule: | |
| I | 500 mg. |
| Diluent: Sterile Water for Injection | 2 cc. |
| OPTHALMIC SOLUTION | |
| I | 100 mg. |
| Hydroxypropylmethyl Cellulose | 5 mg. |
| Sterile Water | to  1 ml. |
| OTIC SOLUTION | |

| PARENTERAL SOLUTION | PER TABLET |
|---|---|
| I | 100 mg. |
| Benzalkonium Chloride | 0.1 mg. |
| Sterile Water | to  1 ml. |
| TOPICAL OINTMENT | |
| I | 100 mg. |
| Polyethylene Glycol 4000 U.S.P. | 400 mg. |
| Polyethylene Glycol 400 U.S.P. | 1.0 gram |

What is claimed is:

1. A compound having the structure:

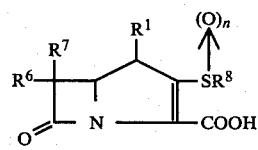

wherein: $R^1$, $R^6$, $R^7$ and $R^8$ are independently selected from the group consisting of hydrogen, ($R^1$ is not H) substituted and unsubstituted: alkyl, alkenyl, and alkynyl, having from 1–10 carbon atoms; cycloalkyl, cycloalkylalkyl, and alkylcycloalkyl, having 3–6 carbon atoms in the cycloalkyl ring and 1–6 carbon atoms in the alkyl moieties; phenyl; aralkyl, aralkenyl and aralkynyl wherein the aryl moiety is phenyl and the alkyl chain has 1–6 carbon atoms; wherein the substituents or substituents relative to the above-named radicals are selected from the group consisting of: amino, mono-, di-, and trialkylamino, hydroxyl, alkoxyl, sulfamoyl, amidino, guanidino, nitro, chloro, bromo, fluoro, cyano and carboxy; and wherein the alkyl moieties of the above-recited substituents have 1–6 carbon atoms; n is 1 or 2.

2. A compound according to claim 1 wherein $R^1$ is alkyl, phenyl, benzyl or cycloalkyl.

3. A compound according to claim 1 wherein $R^6$ is H or methyl and $R^7$ is alkyl, phenyl, aralkyl or hydroxyl-substituted alkyl, phenyl or aralkyl.

4. A compound having the structure:

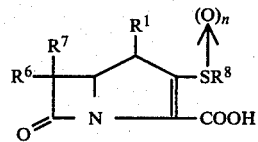

wherein: n is 1; $R^6$ is hydrogen or methyl and $R^8$ is selected from the group consisting of:

H,
$CH_3$,
$(CH_2)_2NH_2$,
$C(CH_3)_2CH_2NH_2$, $$C(CH_3)_2CH_2NH-\overset{NH}{\underset{\parallel}{C}}-H,$$

$$C(CH_3)_2CH_2NH-\overset{NH}{\underset{\parallel}{C}}-CH_3,$$

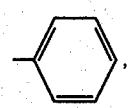,

-continued
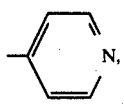
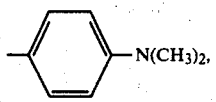
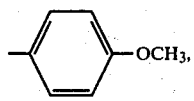
CH₂CH₂CH₂NH₂,
CH₂CH(CH₃)NH₂,
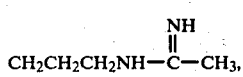
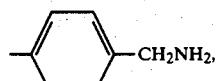
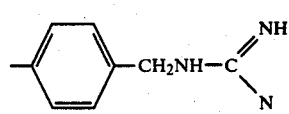
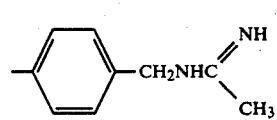
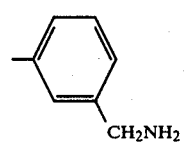
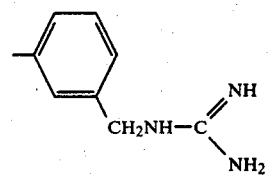
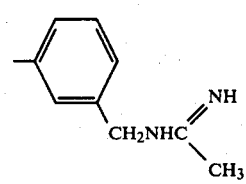
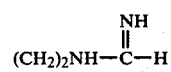
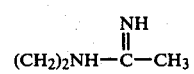
-continued
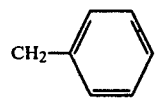
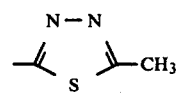
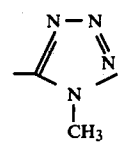
CH(CH₃)CH₂NH₂,
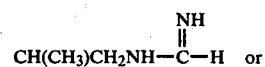
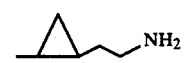
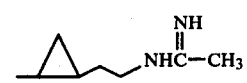
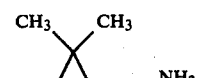
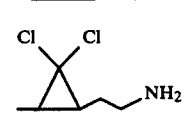
R⁷ is selected from:
—CH₂OH
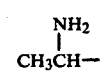
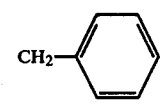

-continued

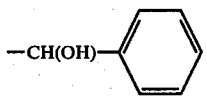

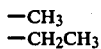

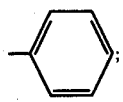

and $R^1$ is independently selected from the group consisting of substituted and unsubstituted: alkyl, alkenyl, and alkynyl, having from 1–10 carbon atoms; cycloalkyl, cycloalkylalkyl, and alkylcycloalkyl, having 3–6 carbon atoms in the cycloalkyl ring and 1–6 carbon atoms in the alkyl moieties; phenyl; aralkyl, aralkenyl, and aralkynyl wherein the aryl moiety is phenyl and the alkyl chain has 1–6 carbon atoms; wherein the substituent or substituents relative to the above-named radicals are selected from the group consisting of: amino, mono-, di-, and trialkylamino, hydroxyl, alkoxyl, sulfamoyl, amidino, guanidino, nitro, chloro, bromo, fluoro, cyano and carboxy; and wherein the alkyl moieties of the above-recited substituents have 1–6 carbon atoms.

5. A compound according to claim 4 wherein $R^1$ is methyl, ethyl, isopropyl, phenyl, benzyl, cyclopropyl, or cyclopropylmethyl.

6. A compound according to claim 1 wherein $R^6$, $R^7$ and $R^8$ are independently selected from the group consisting of hydrogen, substituted and unsubstituted: alkyl, alkenyl, and alkynyl, having from 1–10 carbon cycloalkyl, cycloalkylalkyl, and alkylcycloalkyl, having 3–6 carbon atoms in the cycloalkyl ring and 1–6 carbon atoms in the alkyl moieties; phenyl; aralkyl, aralkenyl, and aralkynyl wherein the aryl moiety is phenyl and the alkyl chain has 1–6 carbon atoms; wherein the substituent or substituents relative to the above-named radicals are selected from the group consisting of: amino, mono-, di- and trialkylamino, hydroxyl, alkoxyl, sulfamoyl, amidino, guanidino, nitro, chloro, bromo, fluoro, cyano and carboxy; and wherein the alkyl moieties of the above-recited substituents have 1–6 carbon atoms; and $R^1$ is selected from the group consisting of methyl, ethyl, propyl, isopropyl cyclopropyl, phenyl and benzyl.

7. An antibiotic pharmaceutical composition comprising a therapeutically effective amount of a compound according to claim 1 and a pharmaceutical carrier therefor.

8. A method of treatment comprising administering an antibacterial effective amount of a compound according to claim 1.

* * * * *